US00PP14617P39

(12) United States Plant Patent
Luby et al.

(10) Patent No.: US PP14,617 P3
(45) Date of Patent: Mar. 23, 2004

(54) GRAPE PLANT NAMED 'LA CRESCENT'

(50) Latin Name: *Vitis vinifera*
Varietal Denomination: La Crescent

(75) Inventors: James Luby, St. Paul, MN (US); Peter Hemstad, Edina, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 241 days.

(21) Appl. No.: 09/829,302

(22) Filed: Apr. 9, 2001

(65) Prior Publication Data

US 2003/0009798 P1 Jan. 9, 2003

(51) Int. Cl.[7] ..... A01H 5/00

(52) U.S. Cl. ..... Plt./207

(58) Field of Search ..... Plt./205, 207

(56) References Cited

U.S. PATENT DOCUMENTS

PP13,309 P2 * 12/2002 Clark et al. ..... Plt./205

* cited by examiner

*Primary Examiner*—Anne Marie Grunberg
(74) *Attorney, Agent, or Firm*—Fish & Richardson P.C., P.A.

(57) ABSTRACT

The invention is a new and distinct variety of grapevine designated 'La Crescent', which has a combination of outstanding wine quality and cold hardiness.

1 Drawing Sheet

Botanical classification: *Vitis vinifera.*
Variety denomination: 'La Crescent'.

BACKGROUND OF THE INVENTION

Grape is one of the most widely planted and economically important fruit crops in the world. Currently, worldwide planting of grapevines exceeds 8.7 million hectares producing 60 million tons annually, with approximately 70% of the grapes being fermented into wine, 28% used for fresh fruit and the remainder used for dried raisins. In the U.S. alone, the grape crop is worth approximately $3 billion annually Most grape varieties used for production of high quality wines are of the species *Vitis vinifera*. The discovery of winemaking, as well as the domestication of the wine grape, likely began in southern Caucasia (presently northwestern Turkey, northern Iraq, Azerbaijan and Georgia) at least 6000 years ago. Eventually, varieties of *V. vinifera* were cultivated throughout the Mediterranean region, then into Europe and Asia, and, ultimately, through European colonization to North America, South America and Australia. On all these continents, successful production of *V. vinifera* occurs predominantly in temperate climate zones similar to that of the indigenous range of *V. vinifera* in Eurasia, e.g., summers that are sunny, warm, and dry, and winters that are mild and rainy. *V. vinifera* varieties cultivated in northern regions of the United States with a continental climate are often subject to serious injury or death from low temperatures during winter. Although several wild Vitis species occur in colder regions of North America and eastern Asia, the wine made from these species generally has serious defects. Thus, there is a need for grape varieties that are winter hardy, yet produce fruit capable of yielding high quality wine.

BRIEF SUMMARY OF THE INVENTION

'La Crescent' is a variety of grape (Vitis sp.) that has a unique combination of outstanding wine quality and very high cold hardiness not found in existing grape varieties. Fruit of 'La Crescent' can be fermented to produce white wine having desirable aromas of citrus, apricot, pineapple, and muscat (as found in Riesling or Vignoles varieties) and lacks 'foxy' aromas associated with *V. labrusca* and herbaceous aromas associated with *V. riparia.* As grown in east central Minnesota, the plants of 'La Crescent' plants are moderately vigorous and very winter hardy. The vines are somewhat resistant to phenoxy herbicide injury and moderately susceptible to foliar phylloxera (*Daktulospahira vitifoliae*) damage. Downy mildew, caused by *Plasmopara viticola,* has been observed at moderate levels on the foliage, but has not been seen on the fruit. Powdery mildew disease, caused by *Uncinula necator,* has been seen at low levels on the foliage, but not on the fruit. The disease black rot, caused by *Guignardia bidwellii,* has been observed sporadically and at low levels on the leaves, but not on the fruit. 'La Crescent' vines set a light to moderate crop load that varies from year to year. The fruit are borne on a loose, medium sized cluster. The berries are small to medium sized and amber with a waxy bloom at maturity. In some years, a small percentage of the berries have been observed dropping from the cluster before or during harvest. The berries have not been observed to split, even under wet conditions in the autumn. The fruit at harvest is usually relatively high in sugar and moderate to high in acidity.

BRIEF DESCRIPTION OF THE DRAWINGS

The accompanying color photograph shows characteristics of 'La Cresent' grown under typical field conditions. The photograph depicts color features as true as is reasonably possible.

DETAILED BOTANICAL DESCRIPTION

'La Cresent' arose from a controlled cross as part of the grape breeding program at the University of Minnesota Horticultural Research Center (HRC) in Carver County, Minn. 'La Crescent' was a seedling from the cross designated GE 8824 made in 1988 and having the parentage 'St. Pepin'×'E.S. 6-8-25'. The 'St. Pepin' variety is described in U.S. Pat. No. P.P. 5,771. The 'E.S. 6-8-25' variety is an unnamed selection resulting from a *V. riparia*×'Muscat Hamburg' cross. 'La Crescent' was selected as an initial seedling vine at location Block 1 Row 19 Post 9.9 at the HRC in 1992. A total of 11 vines of 'La Crescent' were asexually propagated by hardwood cuttings and planted at the HRC as follows: 3 plants were planted in 1995 in Block 10 Row 8; 5 plants were planted in 1997 in Block 18 Row 8; 2 plants were planted in 1998 in Block 20 Row 3; and 1 plant was planted in 1999 in Block 1 Row 19. These plants were observed through 2002, including their fruit, and were indistinguishable in appearance from the original 'La Crescent' seedling. Therefore, the progeny of 'La Crescent' are stable and reproduced true to type in successive generations.

'La Crescent' has perfect flowers containing extended stamens with anthers having viable pollen, whereas the 'St. Pepin' parental variety has functionally pistillate flowers (female only) with reflexed stamens having anthers with inviable pollen. When ripe, the berries of 'LA Crescent' are yellow-amber and contain little or no anthocyanin pigment, whereas the 'E.S. 6-8-25' parental variety produces highly pigmented dark blue berries.

The following data pertains to vines grown at the University of Minnesota Horticultural Research Center in Carver County, Minn. near Excelsior. For comparison purposes, data were collected for certain morphological descriptors from plants and fruit of the variety Seyval, a grape variety commonly grown in Minnesota and the eastern U.S. for the production of white wine. Seyval is a parent of 'St. Pepin,' and thus a grandparent of 'La Crescent'. Alphanumeric color designations refer to values based on The R.H.S. Colour Chart published by The Royal Horticultural Society, London, England. Many of the descriptors are based on those set forth by the International Board for Plant Genetic Resources in collaboration with the Office Internationale de la Vigne et du Vin (OIV) and the International Union for the Protection of New Varieties of Plants.

When dimensions, sizes, colors and other characteristics are given, it is to be understood that such characteristics are approximations set forth as accurately as possible. Variations of the usual magnitude incident to climatic factors, fertilization, pruning, pest control and other cultural practices are to be expected.

A) Mature Canes

The values presented are the means (with ranges in parentheses) of 10 canes observed from the 2000 growing season.

| | |
|---|---|
| 1. Diameter at base: | 9.0 cm (7.8–11.7) |
| 2. Diameter at midpoint: | 7.1 cm (4.8–8.8) |
| 3. Color of canes: | striated, yellowish brown RHS color chips 175A, 175B, 175C |
| 4. Internode length at base: | 2.7 cm (1.9–4.0) |
| 5. Internode length at midpoint: | 12.2 cm (7.7–15.3) |
| 6. Lenticels present: | no |
| 7. Cane cross-section shape: | elliptical |
| 8. Density of hairs on mature cane: | very sparse to none |
| 9. Average total cane length: | variable |
| 10. Tendril pattern on shoot: | 2,0,2,0 etc. (two nodes with a tendril followed by one node without) |
| 11. Tendrils forked: | yes, one side usually forked twice |
| 12. Tendril texture: | striated |
| 13. Tendril length: | 17 cm (12–24) |
| 14. Bud width: | 5.3 mm (4.1–6.4) |
| 15. Bud shape: | triangular |

B) Trunk

| | |
|---|---|
| 1. Bark texture | moderately flaky, segments approx. 12 cm. long (variable) |
| 2. Bank color | about 201C |

C) Mature Leaves

Ten representative mature leaves from above the clusters in the middle third of the shoot were examined. The leaves were pressed and dried for later analysis. The values presented below are means (with ranges in parentheses) from collections in September 2000 or June 2003. Descriptors of mature leaves, including the designations N1 through N5, relate to "OIV—Code Numbers 065–093" of *Preliminary Minimal Descriptor List for Grapevine Varieties* (Dettweiler E., 1991, Institüt fur Rebenzüchtung, Geilweilerhof, Germany).

| | 'La Crescent' | Seyval |
|---|---|---|
| 1. Length of blade: | 13.0 cm (10.1–16.0) | 14.1 cm (12.5–15.0) |
| 2. Width of blade: | 11.5 cm (9.2–13.3) | 12.3 cm (11.1–13.4) |
| 3. Shape of blade: | cuneiform | cordate-circular |
| 4. Number of lobes: | 3.7 (3–5) | 2.7 (0–5) |
| 5. Length of vein N1: | 10.3 cm (8.2–12.1) | 10.0 cm (9.3–11.3) |
| 6. Length of vein N2: | 8.6 cm (6.5–10.1) | 8.5 cm (7.2–10.5) |
| 7. Length of vein N3: | 5.4 cm (3.8–6.8) | 6.1 cm (5.3–7.4) |
| 8. Length of vein N5: | 1.4 cm (0.7–2.3) | 2.6 cm (1.5–3.3) |
| 9. Length of N2 teeth: | 13.4 mm (9–19) | 14.8 mm (9–22) |
| 10. Width of N2 teeth: | 13.7 mm (9–19) | 14.4 mm (9–19) |
| 11. Length/width ratio of N2 teeth: | 0.98 (0.8–1.2) | 1.04 (0.8–1.5) |
| 12. Length of N4 teeth: | 6.6 mm (5–9) | 7.2 mm (4–11) |
| 13. Width of N4 teeth: | 8.7 mm (7–10) | 10.8 mm (7–15) |
| 14. Length/width ratio of N4 teeth: | 0.76 (0.6–1.0) | 0.67 (0.4–0.9) |
| 15. Shape of teeth: | rectilinear, some convex | convex |
| 16. Shape of petiolar sinus: | open | lobes slightly overlapping |
| 17. Shape of base of petiolar sinus: | u-shaped | v-shaped |
| 18. Depth of petiolar sinus: | 22.1 mm (17–29) | 25.9 mm (18–35) |
| 19. Width of petiolar sinus: | 22.9 mm (14–37) | 10.3 mm (6–15) |
| 20. Length of petioles: | 6.6 cm (4.5–8.6) | 8.8 cm (6.5–11.0) |
| 21. Pubescence on adaxial surface: | sparse on veins and petioles, none at vein junctions | |
| 22. Pubescence on abaxial surface: | abundant at main vein junctions and at petiolar junction | |
| 23. Pubescence on leaf surface: | moderately dense pubescence on main veins and at petiolar junction on abaxial surface, sparse pubescence on main veins on adaxial surface, slight pubescence on petiole | |
| 24. Color of adaxial leaf surface: | 146A, yellow green, veins near petiolar sinus can be tinged with anthocyanin; young leaves are tinged with anthocyanin on adaxial surface | |
| 25. Color of adaxial leaf surface: | 146B, yellow green | |
| 26. Color of leaf petiole: | 146C, yellow green, can be striped with anthocyanin on surfaces exposed to direct sunlight | |

D) Flowers

| | |
|---|---|
| 1. Fragrance: | moderately fragrant |
| 2. Mean time of flowering: | June 14 when grown in Excelsior, Minnesota |

-continued

| | |
|---|---|
| 3. Color of petal: | 145A, yellow, green |
| 4. Color of sepal: | 144A, yellow, green |
| 5. Color of pollen: | 4B, yellow |
| 6. Petal number: | 5, fused in calyptra |
| 7. Petal shape: | cohering at summit and separating at base: 2.5 mm long; 1 mm wide at fused end; reflexed after dehiscence from flower |
| 8. Shape of cluster: | somewhat conical, typically with one wing, large clusters may exhibit bifurcated distal end |
| 9. Size of cluster: | 14.7 cm long (range 12.5–17.6); 8.1 cm wide (range 5.6–11.5) |
| 10. Number of flowers per cluster: | 347 (range 233–429) |
| 11. Size of individual entire flower: | 7.5 mm long; 4.6 mm wide |
| 12. Pollen fertility: | yes, based on use in controlled pollinations |
| 13. color of stamen: | Anther: 162C, grayed-yellow<br>Filament: 155A, white |
| 14. Stamen number: | 5.6 (range 5–7) |
| 15. Pistil number: | 1 per flower |
| 16. Pistil length: | 2.6 mm |
| 17. Color of pistil: | 144A, yellow-green |

E) Fruit

The values presented below are means (with ranges in parentheses) from fruit observed in the 2000 growing season, except for those traits indicated (**), which are means from the 1995, 1999, and 2000 growing seasons.

| | 'La Crescent' | Seyval |
|---|---|---|
| 1. Cluster length: | 14.7 cm (12.5–17.6) | 12.1 cm (9.0–15.1) |
| 2. Cluster weight:** | 86.8 g (53.6–167.9) | 144.2 g (92.4–222.3) |
| 3. Cluster density: | loose | medium |
| 4. Berry weight:** | 1.30 g (1.10–1.66) | 1.90 g (1.59–2.22) |
| 5. Berry length: | 12.8 mm (11.5–14.2) | 13.8 mm (12.2–15.4) |
| 6. Berry diameter at equator: | 12.4 mm (11.5–14.0) | 13.3 mm (12.1–15.3) |
| 7. Berry shape: | roundish | roundish |
| 8. Berry cross–section: | circular | circular |
| 9. Berry, color of skin: | yellow-amber about 161A | greenish-yellow about 160A |
| 10. Berry, color of flesh: | light green, nearly clear, 160C | light green, nearly clear |
| 11. Berry, particular flavor: | apricot | neutral |
| 12. Length of pedicel: | 4.5 mm | 6.2 mm |
| 13. Berry, separation from pedicel: | easy | difficult |
| 14. Berry, presence of seeds: | fully developed | fully developed |
| 15. Seed number/berry: | 2.3 (1–4) | 2.2 (1–4) |
| 16. Seed length: | 0.57 mm (0.48–0.65) | 0.59 mm (0.54–0.65) |
| 17. Seed width: | 0.31 mm (0.26–0.37) | 0.39 mm (0.35–0.46) |
| 18. Seed length/width ratio: | 1.84 | 1.51 |
| 19. Seed weight: | 0.020 g | 0.031 g |
| 20. Seed color: | varies from about N200A to about N200B | about 177A |

F) Harvest Parameters

Values represent the means (with ranges in parentheses) for fruit harvested over six growing seasons (1994, 1996–2000) for 'La Crescent' and four growing seasons (1995, 1996, 1999, 2000) for Seyval.

| | 'La Crescent' | Seyval |
|---|---|---|
| 1. Harvest date: | 9/26 (9/16–10/5) | 9/27 (9/16–10/6) |
| 2. Brix: | 24.5° (22.6°–27.6°) | 20.9° (18.6°–23.2°) |
| 3. pH: | 3.00 (2.63–3.15) | 3.15 (2.91–3.41) |
| 4. % titratable acidity: | 1.19% (0.93–1.57%) | 0.89% (0.80–1.02%) |

G) Vineyard Performance

Based on observations compiled over 9 years (1992–2000).

| | |
|---|---|
| 1. Susceptibility to powdery mildew (*Uncinula necator*): | low |
| 2. Susceptibility to downy mildew (*Plasmopara viticola*): | moderate |
| 3. Susceptibility to black rot (*Guignardia bidwellii*): | low |
| 4. Susceptibility to bunch rot (Botrytis, etc): | very low |
| 5. Susceptibility to foliar phylloxera (*Daktulospahira vitifoliae*): | moderate |
| 6. Susceptibility to Crown gall (*Agrobacterium tumefaciwns*): | no natural infection observed |
| 7. Susceptibility to phenoxy herbicide drift (e.g., 2,4-D): | low |
| 8. Berry splitting: | none observed |
| 9. Berry shelling: | slight to moderate |
| 10. Vigor level: | moderate |
| 11. Winter hardiness: | high, trunks have survived −38° C. |
| 12. Wood ripening: | good |

H) Wine Quality

Descriptions below are compiled from observations on wine made from 'La Crescent' fruit harvested during the 1994–2000 growing seasons.

| | |
|---|---|
| 1. Flavors and aromas: | apricot, citrus (grapefruit, tangerine), pineapple, muscat; no 'hybrid', berbaceous, or labrusca aromas |
| 2. Balance: | good body, well balanced when finished with residual sugar |
| 3. Color: | attractive golden yellow |
| 4. Propensity for oxidation: | low |
| 5. Overall quality: | excellent, reminiscent of Riesling or Vignoles |

What is claimed is:

1. A new and distinct variety of grapeplant designated 'La Crescent' as described and illustrated herein.

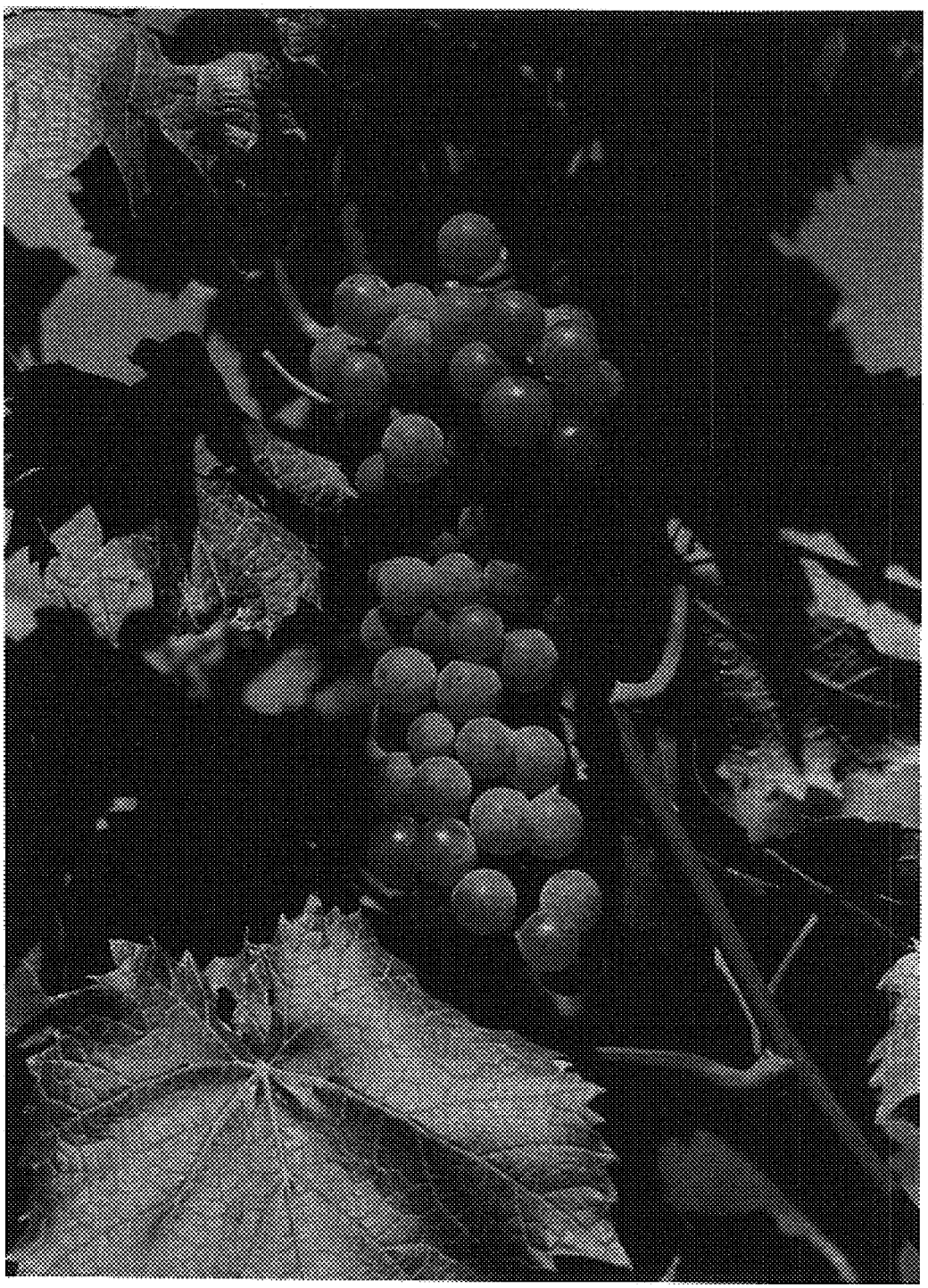

* * * * *